United States Patent [19]

Stephen

[11] 4,335,352

[45] Jun. 15, 1982

[54] YIELD STRENGTH DETERMINATION OF FERROMAGNETIC MATERIALS

[75] Inventor: David D. Stephen, Houston, Tex.

[73] Assignee: Homco International Inc., Houston, Tex.

[21] Appl. No.: 102,790

[22] Filed: Dec. 12, 1979

[51] Int. Cl.³ ............ G01R 33/12; G01N 27/72; B07C 5/344

[52] U.S. Cl. ............... 324/228; 209/567; 324/227; 324/239

[58] Field of Search ............... 324/200–202, 324/205, 206, 210–212, 222, 226–228, 232, 233, 234, 239, 243; 209/3.1, 567–570

[56] References Cited

U.S. PATENT DOCUMENTS

| | | | |
|---|---|---|---|
| 2,677,802 | 5/1954 | Irwin | 324/232 |
| 2,822,088 | 2/1958 | Beaumont et al. | 324/200 |
| 3,432,747 | 3/1969 | Quittner | 324/239 |
| 3,434,048 | 3/1969 | Law et al. | 324/239 |
| 3,475,681 | 10/1969 | Nerwin et al. | 324/243 X |
| 3,478,876 | 11/1969 | Littwin et al. | 209/3.1 |
| 3,586,164 | 6/1971 | Pool | 209/3.1 |
| 4,058,763 | 11/1977 | Steingroever | 209/567 X |
| 4,083,002 | 4/1978 | Allport | 324/227 |

OTHER PUBLICATIONS

Kraska et al., Eddy Current Measurement of Magnetic Flux Density, *Tech. Report AFML-TR-72-115*, May 1972, Air Force Systems Command, pp. 1–27.
Staffin, Robt., 6 Ways to Measure Phase Angle *Control Engineering*, Oct. 1965, pp. 78–83.

*Primary Examiner*—Gerard R. Strecker
*Attorney, Agent, or Firm*—Edward J. Cabic

[57] ABSTRACT

This invention pertains to two forms of verifier of the grade of oil field tubular goods. The first form can be thought of as a sorter in that it will indicate when a particular length of tubular goods is of a different grade than its companions in a lot. The second form will identify the grade of a length. Both forms depend upon magnetizing or inducing magnetic eddy currents in the pipe which are detected and handled by the invention circuitry to sort or to identify.

28 Claims, 4 Drawing Figures

YIELD STRENGTH DETERMINATION OF FERROMAGNETIC MATERIALS

This invention pertains to non-destructive measurement of the properties of materials, and more specifically the measurement of the magnetic properties of ferrous materials.

Still more in particular, the invention concerns two forms of devices pertaining to the grade of oil field tubular goods. In the drilling of wells and the handling of petroleum hydro-carbon materials, large numbers of different types of pipe are used. For example, line pipe is used to convey crude oil from the well to collection points, drill pipe is used in the drilling of wells, casing is used at interim levels in drilling, tubing is used to produce the fluids from wells, and many other kinds of pipe are used in the oil field. Each of these different types of pipe is available in different sizes and grades. When pipe is new, it is of course graded by the mill or factory producing it. But tubular goods are frequently reused many times, and in this process different pipes can be mixed together, especially where they are the same size. Having the wrong grade pipe among a lot of pipes can cause problems. Thus, the sorting of tubular goods according to grade, and the verifing of the grade of a particular piece of tubular goods, are important problems in the oil field.

The invention measures the magnetic properties of ferrous materials. In oil field tubular goods, these magnetic properties correspond to yield strength. That is, different yield strengths produce different unique magnetic properties. The so called "grade" of these oil field tubular goods is in fact a statement of their yield strength. Thus, by measuring their magnetic properties, one can determine the grade of the tubular goods. Grade has been standardized and defined by the American Petroleum Institute, see API standard No. 2-100, revised to December 1958. Basically, the higher, more desirable grades have higher yield strengths.

Yield strength or grade depends on chemical composition, mechanical working, and especially the heat treatment of the steel. Each grade will produce a unique magnetization response curve, and thus different grades can be discriminated based on these unique characteristics. Using the invention methods and apparatus, an electronic response is generated which is dependent only on these magnetic properties.

In this manner, invention instruments operate on the grade of the tubular goods, and do so independently of nominal wall thickness, outside diameter, cross-sectional geometry, overall length, upsets and other disturbances on the surface, and the like. That is, the invention responds solely to the magnetic characteristics of the tubular goods, thus operating directly on its yield strength and thus its grade.

Many of the prior art grade identifiers which operate on magnetic principles use a single measurement. All such systems are highly unreliable because a set of values or a curve must be extrapolated from a single measured value. This is not done in the invention; two values are measured and a curve is extrapolated from two points, which is inherently a much more reliable and accurate method of determining magnetic properties, and thus the yield strength, and thus the grade.

Prior art instruments have many disadvantages, among the primary ones of which are that they require destruction of samples, they are not independent of wall thickness or size, and they are detrimentally affected by configuration, including couplings, threads, upsets and the like which may be on different pieces of tubular goods. Such prior devices include bridge type instruments wherein the length itself forms a leg of the bridge, which is highly undesirable because the results are dependent upon a summation of amplitude and phase, and therefore do not as closely correlate to grade as do the invention's results.

The sorter or type I embodiment of the invention uses a single coil to magnetize or induce eddy currents in the pipe and then to take a reading. The reading is then handled in the electronics of the invention to indicate when a particular piece of pipe is different from all of its companions in the rack or lot of pipe in which it is located. An assumption is made, and the assumption has been found to be reliable, that a rack of pipe will all be at the same state of magnetization because the entire rack is subjected to the same outside magnetic forces, the same sun spots, the same orientation with respect to gravity in the earth's field, the same passing electronic influences, and so forth. Thus, the first embodiment of the invention will determine when a particular piece of pipe is of a different grade than all of its companions, but it will not specifically quantify grade per se.

The type II second embodiment is a true grade identifier. Its basic modus operandi is a two point measurement. The pipe is first "cleaned" of magnetism, the "cleaned" state is measured, the pipe is then subjected to a known magnetization, and the response to this magnetic state is measured. This produces two points as to that particular length, which two points are made to correlate, using known curves of magnetic response for particular grades (yield strengths) to thus determine the grade of each pipe run through the apparatus. Many parts of the same apparatus and circuitry used in type I are also used in the type II.

In type II, absolute magnetic reluctance of the pipe is measured, and thus wall thickness and other physical characteristics of the pipe are not a factor. Using bridges and other single point devices as in the prior art, produces results highly dependent upon wall thickness, surface anomalies, and the like, all of which disadvantages are avoided in the invention.

Thus, the type I form of the invention is a sorter, picking the tubular goods of a different grade than the bulk of the rack. The type II is a true grade identifier.

In both cases, it is the nature of tubular goods that the grade will vary slightly within a particular length of pipe. This is so because hardness or yield strength is determined in large measure by the speed of cooling during heat treatment of the pipe. Since the ends cool more quickly than the middle of the pipe, the ends will generally have a higher yield strength than the middle. To accommodate this slight variation, adjustable alarm cut-off points are provided in the electronics of the invention.

In addition, the output signal can be used to drive alarm means of different sorts, an audible alarm being provided in the preferred embodiment, which operates together with upper and lower trip points, so that the variation within a grade can be accommodated without alerting the operator to minor irregularities. This is applicable, with slight modification, to both the type I and type II variations of the invention.

The invention is not limited to operation with oil field tubular goods. Since it measures magnetic properties of ferrous materials, it can be used for all sorts of pipe, other forms of steel, and in other environments.

The above and other advantages of the invention will be pointed out or will become evident in the following detailed description and claims, and in the accompanying drawings also forming a part of the disclosure, in which:

Figure 1:
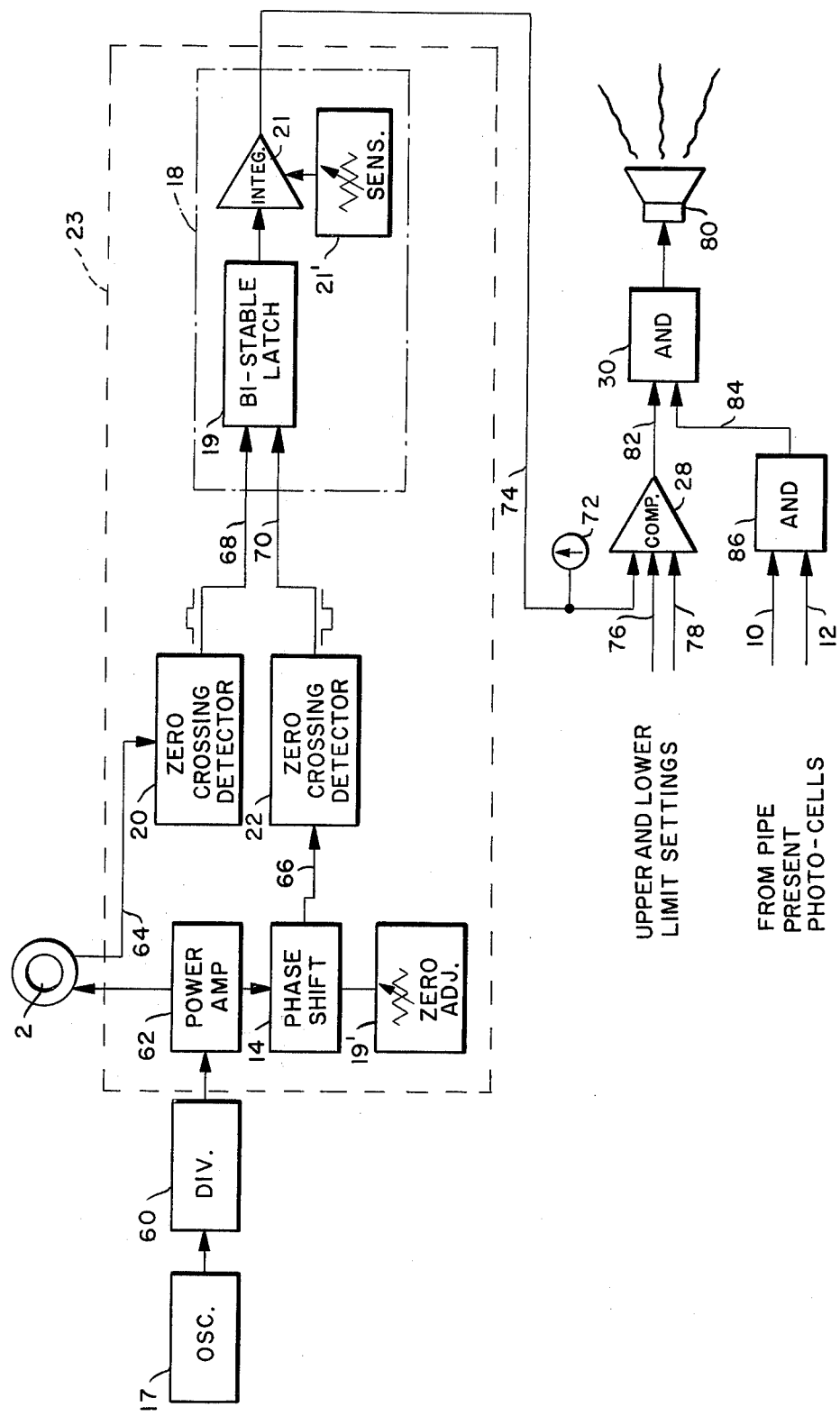
FIG. 1 is an electrical schematic diagram of a first form of the invention.
Figure 1A:
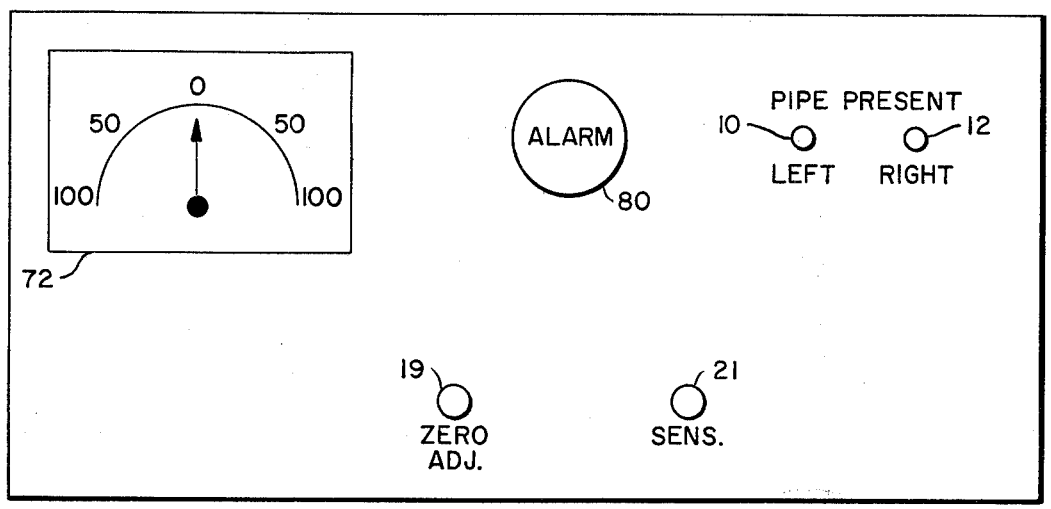
FIG. 1A is the front panel of an instrument embodying the circuit of FIG. 1.

Referring now to FIGS. 1 and 1A, there is shown the type I form of the invention which is used to identify a piece of tubular goods different from its companions without determination of its particular grade. As can be seen by a quick comparison of FIGS. 1 and 2, many parts of the circuitry are common.

The circuitry comprises an oscillator 17 which puts out a very high frequency, in the millions of Hz. The output of the oscillator goes into a divider circuit 60, which feeds into an amplifier 62. The output of the divider is very stable at 60 cycles per second to thus avoid the use of line current frequency, which is highly unstable.

A coil 2 measures the reluctance of the particular pipe. Conventional means are provided to run the pipe through coil 2. This equipment, in common oil field usage, is often trailer mounted, so that the service can come to the well site or other customer location where the pipe is located. It is of course much simplier to drive an instrument trailer out to a pipe yard rather than to move all of the pipe. However, the invention could also be used in a stationary situation as in a steel mill.

Coil 2 is actually a pair of coils arranged in series along the direction of pipe travel, and operates on the transformer effect, that is the amplifier 62 output magnetizes or induces eddy currents in the pipe, the energy is transmitted from the first half of the coil 2 through the pipe and into the second half of the coil 2, and then out on a line 64 to a block 20 in the circuitry. Thus, the pipe, at an unknown state of magnetization, acts to modify the output of amplifier 62 through coil 2 and the pipe and out on line 64. The same output which goes into coil 2 is also delivered to a phase shifter 14, and then on a line 66 to a second component 22 which is identical to the component 20. 20 and 22 are limiter and edge trigger devices or zero crossing detectors which produce the same but opposite signals, as indicated by the notations on their two respective output lines 68 and 70.

The invention depends upon the phase shift which occurs between the signals on the two internal coils in the coil 2 to produce the meaningful results which are of course affected by the state of magnetization of the pipe and its grade.

In use, the operator first zeros the first length going through the apparatus, see meter 72 in FIG. 1A, and thus each successive piece of tubular goods going through the instrument should also produce a zero reading, so long as all of the pipe is of the same grade and so long as each successive piece of pipe is at about the same state of magnetization, the basic assumption of this form of the invention.

Phase shifter 14 is adjustable and permits "tuning" of the two output signals on the line 68 and 70 to achieve the zero condition at the output line 74 of the integrator 21.

The two leads in and out of the coil 2 are selected off of appropriate parts of that coil so that the signals are normally 180° out of phase. Phase shifter 14 causes an inversion as well, and thus the outputs of the edge triggers 20 and 22 are normally 180° out of phase as they feed into bi-stable latch 19.

Latch 19 is half of the larger block 18, which is the phase demodulator of the invention. This block 18 is a unique part of the invention, and is used in both forms. So long as the two inputs on 68 and 70 are exactly out of phase, the meter will remain at rest, at zero for type I and off scale for type II. When one of the inputs shift in phase, as when an out of grade pipe is detected in type I, the latch 19 will then produce an output which is integrated at the integrator 21 and then outputted on a line 74 to the meter 72. The meter needle will then swing to one side or the other which will be meaningful information to the operator indicating that the different piece of pipe is either of a higher or a lower yield strength (grade) than its companions in that rack or lot of pipe.

Thus, so long as the two signals into the bi-stable latch 19 are out of phase, an output signal having a 50% duty cycle, that is 50% up and 50% down, will be produced, integration of which at 21 will produce zero, thus leaving the needle at rest. When an unusual grade pipe goes through the coil 2, this will cause a phase shift at the two inputs to the latch, which will cause a change in its output signals, to, for example, a 75-25% split in one direction. Integrating that output will produce a deflection of the meter in the appropriate direction and of the appropriate magnitude corresponding to the amount by which the duty cycle output of the latch 19 has been upset from its normal 50—50 split.

Since the higher yield strengths are more valuable tubular goods, they are put aside and saved. Pipe of lower grade than the rack may be discarded or used for non-oil field applications, such as for construction. Thus, even though grade is not actually determined by the type I form of the invention, separation into higher or lower grades can be achieved.

More importantly, it thus can be seen that the measuring part of the invention is insensitive to temperature, will not drift, and does not have an ambiguous state because the zero position of the meter is affirmatively set at the 50—50 duty cycle output of the latch which is set in the middle of the digital phase demodulator operating range. Another advantage is that the 50—50 split, or output voltage divided by two point, can start from any voltage, and thus the invention in effect can "move" along a 45° line of output voltages, and thus can accommodate many different kinds and type of pipes and other ferrous materials. That is, the invention operates in a linear region thus producing many well known advantages in addition to those set forth above.

Attention is directed to the dotted line block 23 drawn around a large number of the components described above, starting from amplifier 62 and running to integrator 21, including the phase demodulator 18 enclosed in its own a dash-dot box. This has been done for convenience, in that block 23 in toto will be shown as a single block in FIG. 2 to save drawing effort and corresponding description below.

After meter 72, output line 74 from overall block 23 feeds into a comparator 28. Device 28 compares this signal to a pair of signals 76 and 78 corresponding to the range within which the pipe is permitted to vary as to its magnetic properties before activating the alarm 80. This range accommodates minor irregularities and the differences in grade within a single piece of pipe. These upper and lower limits are voltage standards or tolerances on the amount of meter deflection acceptable. So long as the output on line 74 is within that range, comparator 28 will not output a signal on its output line 82. Alarm 80 is driven directly from an AND gate 30, which AND gate also receives an enable signal on line 84 from AND gate 86. The input to the AND gate 86 is a pair of lines 10 and 12 from a pair of photocells, not shown in FIG. 1, which indicates that pipe is present in the system.

Thus, a signal is always present on line 74, which, under normal conditions will be a zero or logic low, which will, of course, be within the range of the upper and lower limits set on lines 76 and 78. Thus, there is no output on line 82 into AND gate 30. Assuming there is pipe in the system, as detected by the two photocells normally flanking the coil 2 along the direction of pipe travel, then an enable signal on line 84 from AND gate 86 will be present. When an unusual pipe is detected, a signal on line 74 will exceed the range above or below, on the two lines 76 and 78, and an output will appear on line 82, an enable signal will already be present on line 84, and AND gate 30 will operate alarm 80 to alert the operator that the needle has moved out of range.

FIG. 1A shows the front panel of an instrument embodying the circuit of FIG. 1. A pair of LEDs associated with the lines 10 and 12 blink or are otherwise activated to indicate the presence of pipe in the system. The two adjustments 19 and 21 are into the bi-stable latch and integrator respectively to adjust for the zero, as set forth above, and to adjust the sensitivity of the integration performed in the integrator 21.

Figure 2A:
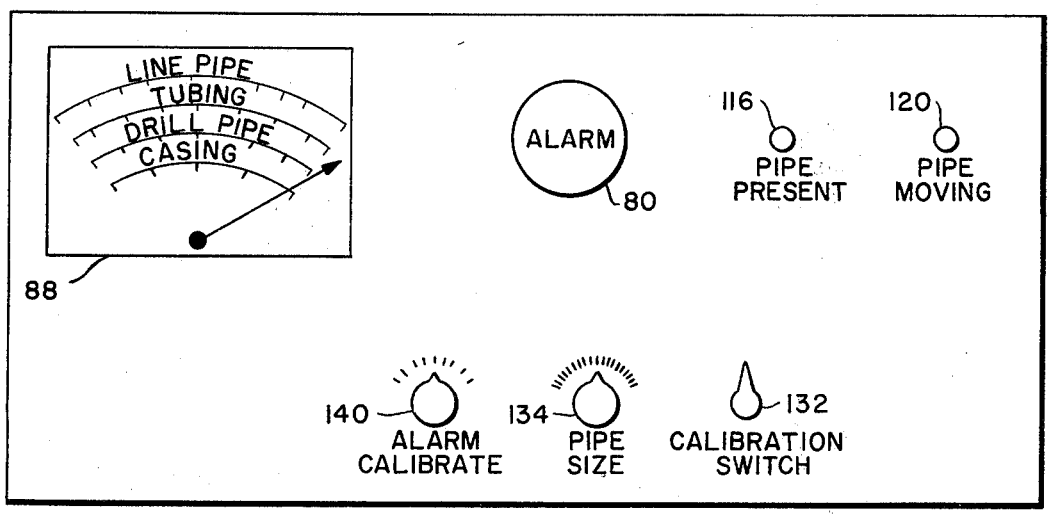
FIG. 2A is the front panel of an instrument embodying the circuit of FIG. 2.
Figure 2:
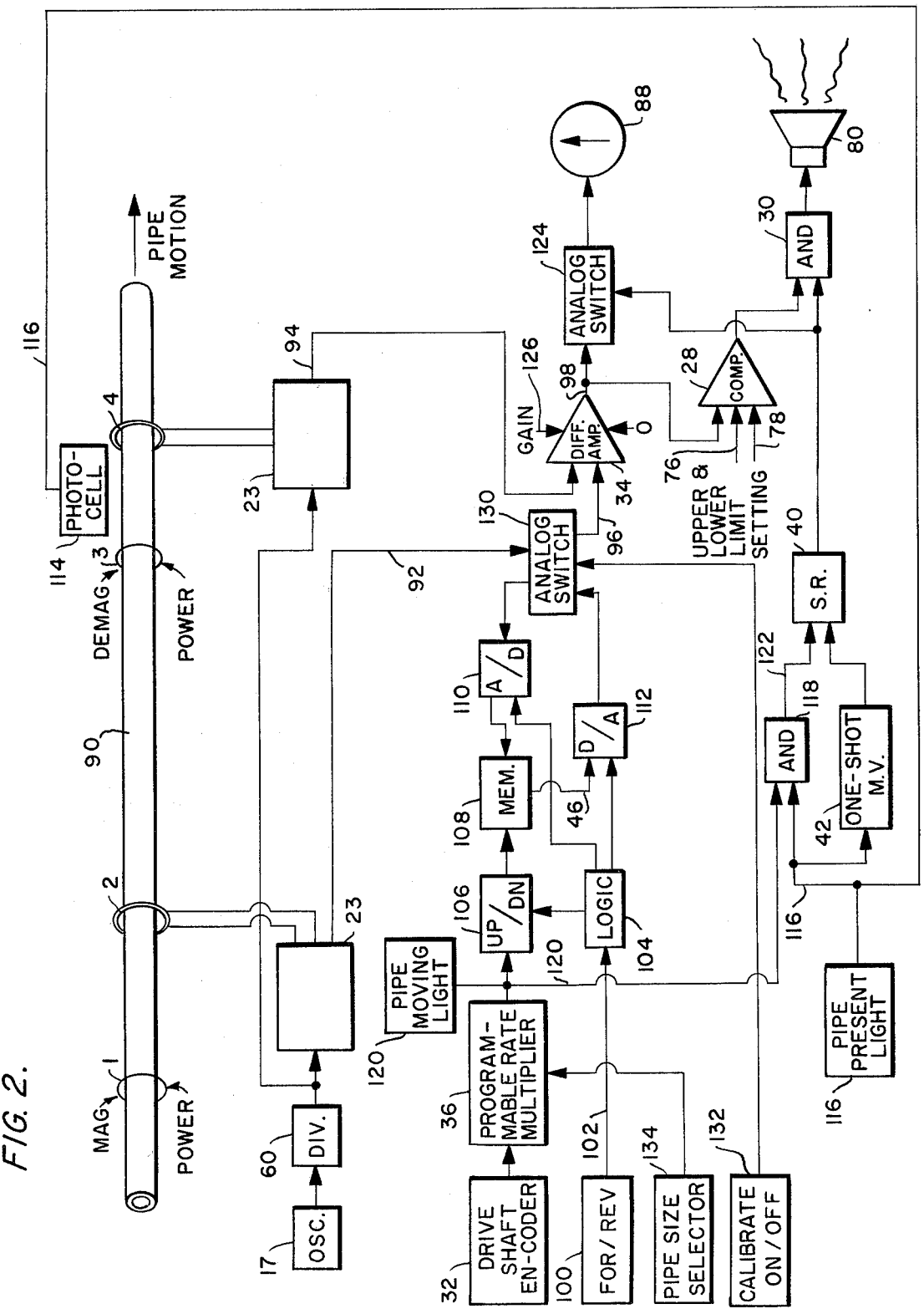
FIG. 2 is an electrical diagram of a second form of the invention.

Referring now to FIGS. 2 and 2A, there is shown a second embodiment of the invention which is a grade identifier as opposed to the sorter of FIG. 1.

The general modus operandi of type II is to: (1) clean the pipe of magnetism; (2) measure the reluctance at that state; (3) subject the pipe to a high static magnetic field to raise the magnetic material to its saturation point; and (4) after removing the field to measure the reluctance at the residual state. In this manner, two points on the curve, that is the demagnetized and the remanence states are both measured, and these two points are used to identify the yield strength and in turn the grade of the pipe, as defined above.

Of course, as is evident to those skilled in the art, other alerting means in addition to the audible alarm 80 could also be driven from AND gate 30, such as flashing lights, remote alerting means for many sorts, and the like.

The study of the magnetic qualities of ferrous materials and especially of tubular goods, is a fairly complex area of science. However, the invention, as will be explained below, in effect is an empirical device in that it has certain characteristics of the types and grades of tubular goods on which it can operate in effect "tabled". This is accomplished primarily by the multiple scales on the meter 88 of FIG. 2A.

The theory underlying the modus operandi of the FIG. 2 form is explained in greater detail in the "Standard Handbook for Electrical Engineers" by Fink and Carroll, 10th edition, McGraw Hill, copyrighted 1969, 1968, and 1957, see pages 4-101 to 4-114 especially the curves found on pages 4-101 and 4-106.

Referring now to FIG. 2, the pipe 90 passes through a set of four coils 1, 2, 3 and 4, the coils 2 and 4 being the same as each other and the same as coil 2 in FIG. 1. The coils 1 and 3 are the same as each other, except that coil 1 is used to magnetized the pipe and coil 3 is used to demagnetize the pipe.

The order indicated; magnetize, read, demagnetize, read; is exemplary only. The reverse situation could occur, that is, the pipe could move from coil 4 to coil 1, and in fact this does occasionally happen, as will be set forth in the operation section below. Further, in the event the trailer in which the invention is mounted includes other equipment which other equipment may already have the pipe magnetized or demagnetized, it may in that case be unnecessary to provide coil 1 or coil 3.

The top end of FIG. 2 is in large measure a duplicate of the top part of FIG. 1, as indicated by the two blocks 23 which each represent block 18 plus the other components indicated in FIG. 1. The two output lines 92 and 94 from the two blocks 23 each corresponds to the line 74 of FIG. 1 with certain changes in concept, as explained in the operation section below.

The two outputs on the lines 92 and 94 go into a linear differential amplifier 34, which is the "heart" of the manner in which the FIG. 2 embodiment determines grade. The line 92 first goes through a series of elements for other purposes described below, before coming out on a line 96 to join line 94 feeding into differential amplifier 34. A differential amplifier is a device which produces an output voltage which is proportional to the difference between its two input voltages. Thus, since the two input voltages are proportional to the states of the pipe magnetized and demagnetized, the output on the line 98 will thus be proportional to the difference, which in turn is proportional to yield strength, which in turn is proportional to the grade of the pipe.

While the two blocks 23 each includes an adjustable phase shifter 14, they are not operated to function in the same manner in FIG. 1 described above. That function, conceptionally, is accommodated by the zero and gain inputs to the differential amplifier 34, as described below.

Shaft encoder 32 is a conventional item attached to the drive mechanism in the instrument moving the pipe 90 through the coils, and it outputs a series of signals, commonly square waves, directly proportional to pipe velocity. More accurately, shaft encoder 32 puts out a signal whenever the mechanism that drives the pipe is in motion. Other means described below indicate pipe presence and thus these two signals together indicate that the pipe is present and is moving through the system.

The rate multiplier 36 provides another adjustment to permit the invention to accommodate itself to different sizes of pinch rollers required to drive different diameter pipes. A larger pipe will move through the same set of pitch rollers faster than a smaller pipe because the smaller pipe will be closer to the center line of the "V notch" in the pinch roller. Thus, the divider block 36 provides an external adjustment to accommodate those conditions.

A forward/reverse switch 100 is located on the operator's panel, and is made to operate in conjunction with the manual switch which reverses the pipe drive means. Thus, a signal indicating forward or reverse will be present on the line 102 feeding into logic block 104.

The array of components between lines 92 and 96 further includes an up/down shift register or counter 106, a memory device 108, a pair of analog to digital and digital to analog interfaces or converters 110 and 112 respectively, and an analog switch 130. Devices 110 and 112 are required because the preferred embodiment of the invention shown operates in a mixed digital and analog mode, as is well known to those skilled in these arts. This same mixed mode logic is also present in the FIG. 1 form of the invention.

The invention includes a photocell 114, the output signal of which on branching line 116 is delivered to an AND gate 118 and one-shot M.V. 42. The other input to AND gate 118 is present on line 120 which is the shaft encoder signal after division in block 36. Thus, an output signal on line 122 indicates that there is pipe present in the system (photocell 114) and that the pipe is moving (encoder 32).

The signals on the lines 116 and 120 also drive indicating LEDs on the front panel carrying the same reference numerals, as shown in FIG. 2A.

Shift register 40 acts, effectively, to put a time delay into the system, which is necessary because it is not physically possible to have the photocell at exactly the same location as the coil 4. By use of this time delay, the optimum physical configuration can be electronically simulated.

The operation of shift register 40 is analogous to the AND gate 86 of FIG. 1, and the components 28–30, 80, 76 and 78 thereafter are exactly analogous.

Finally, the block 124 marked "analog switch" is for presetting the needle of meter 88 to drive the needle off scale so that no arbitrary reading will be obtained. That is, when no pipe is present it is desired that the needle indicate nothing so as to eliminate all possibility of misleading the operator. Such means to bias a meter is of course well within the expertise of those skilled in these arts.

In order to allow for minor grade variation an alarm calibrate adjustment 140 is provided. See also the dial with the same reference numeral in FIG. 2A. The off scale setting indicated in the drawing is factory set.

Control 132, via switch 130, disables blocks 104 through 112 to permit system calibration, as needed.

Memory 108 has 4096 locations, and thus, as will appear more clearly in the operation description below, for each length of pipe, many separate points can be detected and data stored for each.

OPERATION—FIG. 2

The tubular goods are moved with a translational velocity through the equipment from left to right in FIG. 2, thus first encountering coil 1 wherein it is magnetized to a saturated state. For ease of the following description, the first point on the leading edge of the pipe so magnetized will be called point A. Point A next enters coil 2, and the reluctance is detected therein and begins to be stored in memory 108 after passing through blocks 23 and 110. The meter 88 does not yet give any reading because the pipe has not yet entered coil 4, which entry is required to enable the meter to operate. Memory 108 operates like a shift register, and its 4096 memory locations are made to correspond to the physical distance between coils 2 and 4.

The distance between the photo-cell and coil 4 is accommodated by the time delay determined by shift register 40. Thus, as the pipe progresses through the coils, when the point A reaches coil 4, then at that instant both signals will be present on both lines 94 and 96 into the differential amplifier 34, to thereafter output a signal on line 98 to drive meter 88. Thus, the invention is completely independent of real time.

It is possible during normal operation that the operator would reverse the direction of pipe motion after it has gone through some but not all of the four coils. In such case, the meter 88 would be at its off-scale condition because meter 88 has not been enabled by analog switch 124. Further, this backing out of the pipe will not cause any loss of data or confusion of the data whenever it occurs because the forward/reverse switch 100 and the shaft encoder 32 will simply operate in reverse, under the control of the logic block 104 to cause the up/down address device 106 and the memory 108 to back up. Then, when the pipe is driven in the forward direction again, new data will replace the old data as in a tape recorder, and this will continue for any number of times until the photocell 114 enables the rest of the circuit.

The branch of line 98 leading into comparator device 28 functions therein just as the same parts described above in regard to FIG. 1. That is, the alarm 80 will be activated when and only if the signal is out of the tolerances defined by the signals present on lines 76 and 78. Shift register 40 provides an enable signal analogous to AND gate 86 of FIG. 1, but is position rather than time dependent.

The one shot mono-stable M.V. 42 resets the shift register on the trailing edge of the pipe readying the delay for next pipe.

While the invention has been described in detail above, it is to be understood that this detailed description is by way of example only, and the protection granted is to be limited only within the spirit of the invention and the scope of the following claims.

I claim:

1. A method of determining the magnetic qualities of a ferrous material by comparing them to the magnetic qualities of known ferrous materials for identification of said ferrous material comprising the steps of generating signals corresponding to a magnetized state and a demagnetized state of said ferrous material, feeding said signals into a differential amplifier, supplying the output signal of said differential amplifier to indicating means which can have displayed thereon readings obtained from known ferrous materials and which provides a reading, and comparing the reading on said indicating means to readings for known ferrous materials to thereby identify said ferrous material.

2. The method of claim 1, wherein said ferrous material comprises oil field tubular goods, and wherein said tubular goods are moved through a set of coils which perform the various steps of magnetizing, demagnetizing and generating of signals corresponding to said magnetized and said demagnetized states of said tubular goods, each of said signal generating coils being of the type having two internal coil portions with the tubular goods acting as a core between said coil portions in the nature of a transformer, a circuit comprising a source of energy at a predetermined frequency, the method further comprising the steps of supplying said energy to both a first portion of each of said signal generating coils as well as adjustable phase shifting means, supplying the output of the companion portion of each of said coils and the output of said phase shifting means to first and second edge triggering means, adjusting said phase shifting means to zero the instrument so that the outputs of said first and second edge triggering means are equal, opposite and in syncronization with each other, feeding the outputs of said first and second edge triggering means into the inputs of bi-stable latch so that the output of said bi-stable latch will be a 50—50 duty cycle so long as the same type of tubular goods is detected by said coil, supplying the output of said bi-stable latch into an integrator, whereby the output of said integrator will be zero so long as the two inputs to said bi-stable latches remain equal, opposite, and in synchronization and whereby the output of said integrator will vary in proportion to the change in duty cycle input from said 50—50 duty cycle corresponding to the change of magnetic qualities of a particular piece of tubular goods measured by a particular one of said signal generating coils.

3. The method of claim 2, wherein said predetermined frequency is generated by dividing the output frequency of an oscillator, and wherein said oscillator output frequency is much larger than said predetermined frequency.

4. The method of claim 1, wherein said ferrous material comprises oil field tubular goods, moving the tubular goods through a set of coils for performing steps of magnetizing, demagnetizing and generating signals corresponding to said magnetized and demagnetized states of said ferrous materials, passing each portion of said tubular goods through a first generating signal coil and then through a second generating signal coil, generating a signal proportional to the translational velocity of said tubular goods, generating a signal proportional to the presence of said tubular goods in operative relation to said coils, and feeding said last two mentioned translational velocity and tubular goods present signals into logic and memory circuit means utilizing said logic and memory circuit means acting on one of said magnetized or demagnetized state signal generating means to cause sufficient delay to permit presentation to said differential amplifier in real time of both the said magnetized and demagnetized signals, the differential of which is representative of the absolute magnetic properties of the portion of said tubular good located inside said second generating signal coil.

5. The method of claim 4, causing the memory locations in said memory means to correspond to the physical distance between two selected ones of the coils in said set of coils, said two last mentioned signals causing the generated signals corresponding to one of said magnetized and said demagnetized states to be supplied into said memory means but not into said differential amplifier until a selected point on said tubular goods has moved from the first selected coil to the second selected coil, and causing the signals stored in said memory means to be supplied from said memory means to said differential amplifier after said selected point has reached said second coil.

6. The method of claim 5, and generating a signal proportional to the forward or reverse direction of said motion of said tubular goods with respect to said coils, supplying said forward/reverse signal to said logic and memory circuit means, using said forward/reverse signal to cause the signals stored in said memory means to effectively backup therein whenever the tubular goods move in reverse with respect to said coils and their normal forward direction of motion, whereby the forward and reverse motions of said tubular goods with respect to said coils are electronically simulated in said memory and logic circuit means.

7. The method of claim 1, said indicating means comprising alarm means, supplying the output of said differential amplifier to comparator means, supplying signals to said comparator means proportional to predetermined acceptable limits of said magnetic qualities, and supplying an output signal from said comparator means to operate said alarm means when the output signal from said differential amplifier is outside said limits.

8. The method of claim 1, wherein said ferrous material comprises oil field tubular goods, and wherein said magnetic qualities are proportional to the yield strength of said tubular goods, and wherein said yield strength is proportional to the grade of said tubular goods, and wherein said indicating means comprises a meter having a plurality of scales marked off in various of said grades of said tubular goods.

9. The method of claim 8, and the step of imposing an initial enabling condition bias on said meter to prevent the meter needle from moving until a reluctance comparison is made.

10. A method of determining grade of ferrous materials comprising the steps of subjecting the material to known magnetic energy to induce a state of magnetization therein, measuring the induced state of magnetization of the material, storing values corresponding to said measured state of magnetization, demagnetizing the material, measuring the residual magnetic state of the material after demagnetization, generating signals proportional to said residual state of magnetization, feeding said signals corresponding to said magnetized state and to said demagnetized state into a differential amplifier, outputting the signal from said differential amplifier into indicating means, calibrating said indicating means to indicate different grades of goods being measured, and adjusting said differential amplifier so that said output signal will correspond to the grades of a predetermined type of said ferrous materials.

11. Apparatus for determining grade of ferrous materials comprising means for subjecting the material to known magnetic energy to induce a state of magnetization therein, means for measuring the induced state of magnetization of the material, means for storing values corresponding to said measured state of magnetization, means for demagnetizing the material, means for measuring the residual magnetic state of the material after demagnetization, means for generating signals proportional to said residual state of magnetization, means for feeding said signals corresponding to said magnetized state and to said demagnetized state into a differential amplifier, indicating means, means for outputting the signal from said differential amplifier into said indicating means, means for calibrating said indicating means to indicate different grades of goods being measured, and means for adjusting said differential amplifier so that said output signal will correspond to the grades of a predetermined type of ferrous materials.

12. The combination of claim 11, wherein said energy is of a predetermined frequency, an oscillator having an output frequency much larger than said predetermined frequency, and means for dividing the output frequency of said oscillator to produce said predetermined frequency.

13. The combination of claim 11, wherein said ferrous material comprises oil field tubular goods, and wherein said magnetic qualities are proportional to the yield strength of said tubular goods, and wherein said yield strength is proportional to the grade of said tubular goods, and wherein said indicating means comprises a meter having a plurality of scales marked off in various of said grades of said tubular goods.

14. The combination of claim 13, and means for imposing an initial condition bias on said meter.

15. The combination of claim 11, wherein said ferrous material comprises oil field tubular goods, means for moving said tubular goods through a set of coils for performing steps of magnetizing, demagnetizing and generating signals corresponding to said magnetized and demagnetized states of said ferrous material, means for generating a signal proportional to the motion of said tubular goods, means for generating a signal proportional to the presence of said tubular goods when in operative relation to said coils, logic and memory means, means for feeding said last two mentioned motion and tubular goods present signals into said logic and memory means, and means for locating said logic and memory means between the means generating one of said magnetized and demagnetized state signal generating means and said differential amplifier, whereby said circuit may operate independently of real time and responsive only to the position of said tubular goods with respect to said set of coils.

16. The combination of claim 15, wherein the memory locations in said memory means correspond to the physical distance between two selected ones of the coils in said set of coils, means for causing said two last mentioned signals to cause the generated signals corresponding to one of said magnetized and said demagnetized states to be supplied into said memory means but not into said differential amplifier until a selected point on said tubular goods has moved from the first selected coil to the second selected coil, and means for causing the signals stored in said memory means to be supplied from said memory means to said differential amplifier after said selected point has reached said second coil.

17. The combination of claim 16, and means for generating a signal proportional to the foward or reverse direction of said motion of said tubular goods with respect to said coils, means for supplying said foward-/reverse signal to said logic and memory circuit means, means for using said forward/reverse signal to cause the signals stored in said memory means to effectively backup therein whenever the tubular goods move in reverse with respect to said coils and their normal forward direction of motion whereby the forward and reverse motions of said tubular goods with respect to said coils is electronically simulated in said memory and logic circuit means.

18. The method of claim 11, said indicating means comprising alarm means, comparator means, means for supplying the output of said differential amplifier to said comparator means, means for generating and supplying signals to said comparator means proportional to predetermined acceptable limits of said magnetic qualities, and means for supplying an output signal from said comparator means to operate said alarm means when the output signal from said differential amplifier is outside said limits.

19. The combination of claim 11, wherein said ferrous material comprises oil field tubular goods, a set of coils which perform the various steps of magnetizing, demagnetizing and generating of signals corresponding to said magnetized and said demagnetized states of said tubular goods, means to move said tubular goods through said coils, each of said signal generating coils being of the type having two internal coil portions with the tubular goods acting as a core between said coil portions in the nature of a transformer, a source of energy at a predetermined frequency, means for supplying said energy to both a first portion of each of said signal generating coils as well as adjustable phase shifting means, first and second edge triggering means, means for supplying the output of the companion portion of each of said coils and the output of said phase shifting means to said first and second edge triggering means, means for adjusting said phase shifting means to zero the circuit so that the outputs of said first and second edge triggering means are equal, opposite and in syncronization with each other, a bi-stable latch, means for feeding the outputs of said first and second edge triggering means into the opposite inputs of said bi-stable latch so that the output of said bi-stable latch will be 50-50 duty cycle so long as the same type of tubular goods is detected by said coil, an integrator, means for supplying the output of said bi-stable latch into said integrator, whereby the output of said integrator will be zero so long as the two inputs to said bi-stable latch remain equal, opposite, and in synchronization and whereby the output of said integrator will vary in proportion to the shift in duty cycle input to said bi-stable latch corresponding to the change of magnetic qualities of a particular piece of tubular goods measured by a particular one of said signal generating coils.

20. A circuit for determining the magnetic qualities of a ferrous material comprising means to generate signals corresponding to a magnetized state and a demagnetized state of said material, means to compare said signals to each other comprising a differential amplifier, means for feeding said signals into said differential amplifier, indicating means, means for tabling values corresponding to different types of said ferrous materials on said indicating means, and means for supplying the output signal of said differential amplifer to said indicating means, whereby the indicating means provides a reading which can be compared to readings for known ferrous materials to thereby identify said ferrous material.

21. The combination of claim 20, wherein said ferrous material comprises oil field tubular goods, a set of coils which perform the various steps of magnetizing, demagnetizing and generating of signals corresponding to said magnetized and said demagnetized states of said tubular goods, means to move said tubular goods through said coils, each of said signal generating coils being of the type having two internal coil portions with the tubular goods acting as a core between said coil portions in the nature of a transformer, a source of energy at a predetermined frequency, means for supplying said energy to both a first portion of each of said signal generating coils as well as adjustable phase shifting means, first and second edge triggering means, means for supplying the output of the companion portion of each of said coils and the output of said phase shifting means to said first and second edge triggering means, means for adjusting said phase shifting means to zero the circuit so that the outputs of said first and second edge triggering means are equal, opposite and in syncronization with each other a bi-stable latch, means for feeding the outputs of said first and second edge triggering means into the opposite inputs of said bi-stable latch so that the output of said bi-stable latch will be 50-50 duty cycle so long as the same type of tubular goods is detected by said coil, an integrator, means for supplying the output of said bi-stable latch into said integrator, whereby the output of said integrator will be zero so long as the two inputs to said bi-stable latch remain equal, opposite, and in synchronization, and whereby the output of said integrator will vary in proportion to the shift in duty cycle input to said bi-stable latch corresponding to the change of magnetic qualities of a particular piece of tubular goods measured by a particular one of said signal generating coils.

22. The combination of claim 21, an oscillator having an output frequency much larger than said predetermined frequency, and means for dividing the output frequency of said oscillator to produce said predetermined frequency.

23. The combination of claim 20, wherein said ferrous material comprises oil field tubular goods, means for moving said tubular goods through a set of coils including two dual internal coil portions coils for performing steps of magnetizing, demagnetizing and generating signals corresponding to said magnetized and demagnetized states of said ferrous material, means for generating a signal proportional to the motion of said tubular goods, means for generating a signal proportional to the presence of said tubular goods when in operative relation to said coils, logic and memory means, means for feeding said last two mentioned motion and tubular goods present signals into said logic and memory means, and means for locating said logic and memory means between the means generating one of said magnetized and demagnetized state signal generating means and said differential amplifier, whereby said circuit may operate independently of real time and responsive to the position of said tubular goods with respect to said set of coils.

24. The combination of claim 23, wherein the memory locations in said memory means correspond to the physical distance between two selected ones of the coils in said set of coils, means for causing said two last mentioned signals to cause the generated signals corresponding to one of said magnetized and said demagnetized states to be supplied into said memory means but not into said differential amplifier until a selected point on said tubular goods has moved from the first selected coil to the second selected coil, and means for causing the signals stored in said memory means to be supplied from said memory means to said differential amplifier after said selected point has reached said second coil.

25. The combination of claim 24, and means for generating a signal proportional to the forward or reverse direction of said motion of said tubular goods with respect to said coils, means for supplying said forward/reverse signal to said logic and memory circuit means, means for using said forward/reverse signal to cause the signals stored in said memory means to effectively backup therein whenever the tubular goods move in reverse with respect to said coils and their normal forward direction of motion, whereby the forward and reverse motions of said tubular goods with respect to said coils is electronically simulated in said memory and logic circuit means.

26. The combination of claim 20, said indicating means comprising alarm means, comparator means, means for supplying the output of said differential amplifier to said comparator means, means for generating and supplying signals to said comparator means proportional to predetermined acceptable limits of said magnetic qualities, and means for supplying an output signal from said comparator means to operate said alarm means when the output signal from said differential amplifier is outside said limits.

27. The combination of claim 20, wherein said ferrous material comprises oil field tubular goods, and wherein said magnetic qualities are proportional to the yield strength of said tubular goods, and wherein said yield strength is proportional to the grade of said tubular goods, and wherein said indicating means comprises a meter having a plurality of scales marked off in various of said grades of said tubular goods.

28. The combination of claim 27, and means to impose an initial condition bias on said meter.

* * * * *